(12) United States Patent
Kataoka et al.

(10) Patent No.: US 10,232,054 B2
(45) Date of Patent: Mar. 19, 2019

(54) COMPOSITION FOR MRNA DELIVERY

(71) Applicant: AccuRna, Inc., Bunkyo-ku (JP)

(72) Inventors: Kazunori Kataoka, Tokyo (JP); Keiji Itaka, Tokyo (JP); Takehiko Ishii, Tokyo (JP); Hirokuni Uchida, Tokyo (JP); Satoshi Uchida, Tokyo (JP); Miyuki Baba, Tokyo (JP)

(73) Assignee: AccuRna, Inc., Bunkyo-ku (JP)

( * ) Notice: Subject to any disclaimer, the term of this patent is extended or adjusted under 35 U.S.C. 154(b) by 68 days.

(21) Appl. No.: 15/118,407

(22) PCT Filed: Feb. 12, 2014

(86) PCT No.: PCT/JP2014/053190
§ 371 (c)(1),
(2) Date: Sep. 29, 2016

(87) PCT Pub. No.: WO2015/121924
PCT Pub. Date: Aug. 20, 2015

(65) Prior Publication Data
US 2017/0173182 A1   Jun. 22, 2017

(51) Int. Cl.
| | |
|---|---|
| *A61K 48/00* | (2006.01) |
| *A61K 31/7105* | (2006.01) |
| *A61K 38/18* | (2006.01) |
| *A61K 9/00* | (2006.01) |
| *A61K 47/34* | (2017.01) |
| *A61K 31/7115* | (2006.01) |
| *A61K 9/107* | (2006.01) |
| *C12N 15/87* | (2006.01) |
| *A61K 38/17* | (2006.01) |
| *A61K 47/10* | (2017.01) |

(52) U.S. Cl.
CPC ........ *A61K 48/0041* (2013.01); *A61K 9/0019* (2013.01); *A61K 9/1075* (2013.01); *A61K 31/7105* (2013.01); *A61K 31/7115* (2013.01); *A61K 38/1761* (2013.01); *A61K 38/18* (2013.01); *A61K 38/185* (2013.01); *A61K 47/10* (2013.01); *A61K 47/34* (2013.01); *C12N 15/87* (2013.01)

(58) Field of Classification Search
None
See application file for complete search history.

(56) References Cited

U.S. PATENT DOCUMENTS

| | | | | |
|---|---|---|---|---|
| 8,546,487 B2* | 10/2013 | Kataoka | ............... | A61K 9/5192 424/418 |
| 8,710,200 B2* | 4/2014 | Schrum | ............... | A61K 31/7088 536/23.1 |
| 2004/0053228 A1 | 3/2004 | Shibazaki et al. | | |
| 2006/0188490 A1 | 8/2006 | Hoerr et al. | | |
| 2008/0249049 A1 | 10/2008 | Kataoka et al. | | |
| 2009/0258416 A1 | 10/2009 | Kataoka et al. | | |
| 2010/0121043 A1 | 5/2010 | Kataoka et al. | | |
| 2012/0009221 A1 | 1/2012 | Hoerr et al. | | |
| 2012/0053295 A1* | 3/2012 | Kataoka | ............... | A61K 9/5192 525/54.2 |
| 2015/0051347 A1 | 2/2015 | Kataoka et al. | | |

FOREIGN PATENT DOCUMENTS

| | | |
|---|---|---|
| EP | 2 781 536 A1 | 9/2014 |
| JP | 2001-161372 | 6/2001 |
| JP | 2003-271 A | 1/2003 |
| JP | 4535229 B2 | 9/2010 |
| JP | 5061349 B2 | 10/2012 |
| WO | WO 2005/016376 A1 | 2/2005 |
| WO | WO 2006/085664 A1 | 8/2006 |
| WO | WO 2007/099660 A1 | 9/2007 |
| WO | WO 2008/062909 A1 | 5/2008 |
| WO | WO 2013/073697 A1 | 5/2013 |

OTHER PUBLICATIONS

Debus, et al. (2010) "Delivery of messenger RNA using poly(ethylene imine)-poly(ethylene glycol)-copolymer blends for polyplex formation: Biophysical characterization and in vitro transfection properties", Journal of Controlled Release, 148(3): 334-43.*
Liu, et al. (2007) "Recombinant AAV-mediated Expression of Human BDNF Protects Neurons against Cell Apoptosis in Aβ-induced Neuronal Damage Model", Journal of Huazhong University of Science and Technology, 27(3): 233-36.*
Hanson, et al. (2008) "The cellular concentration of Bcl-2 determines its pro- or anti-apoptotic effect", Cell Calcium, 44(3): 243-58.*
International Search Report issued on in PCT/JP2014/053190 (with English translation).
Kazunori Kataoka, "Polymeric Micellar Nanocarriers for Gene and Oligonucleotide Delivery", Molecular Therapy, vol. 21, Suppl. 1, 2013, 1 Page.
Keiji Itaka, et al., "Practical in vivo mRNA delivery via nanomicelles", Antisense, Gene, Delivery Symposium 2012 Processing, 2012, 4 Pages (with English translation).
Connie Cheng, et al. "Multifunctional triblock copolymers for intracellular messenger RNA delivery", Biomaterials, vol. 33, 2012, pp. 6868-6876.
Office Action dated Jan. 30, 2018 in Japanese Patent Application No. 2015-562586.
Keiji Itaka, et al., "Functional recovery of olfactory neuropathy model by in vivo mRNA delivery", Abstracts of the 13th symposium of The Japanese Society of Gene Design and Delivery, No. P27, 2013, p. 38 (with English translation).

(Continued)

*Primary Examiner* — Robert M Kelly
(74) *Attorney, Agent, or Firm* — Oblon, McClelland, Maier & Neustadt, L.L.P.

(57) ABSTRACT

A polyion complex of mRNA and a polycationic polymer, and a composition and a pharmaceutical composition for mRNA delivery are provided. The polyion complex of mRNA and the polycationic polymer can deliver mRNA into cells in the body of a subject almost without inducing inflammation. The polyion complex can then cause mRNA to be uniformly expressed in cells in the body of the subject. The pharmaceutical composition containing the polyion complex is suitable for use in treating a disease whose condition rapidly progresses or an acute disease.

9 Claims, 8 Drawing Sheets

(56) References Cited

OTHER PUBLICATIONS

Akitsugu Matsui, et al., "Introduction of mRNA-encapsulating polymeric nanomicelles into liver by hydrodynamics", Abstracts of the 13$^{th}$ symposium of the Japanese Society of Gene Design and Delivery, No. P25, 2013, p. 36 (with English translation).
Supplemental Partial European Search Report dated Jul. 25, 2017 in Patent Application No. 14882238.0.
Michael S. D. Kormann. et al. "Expression of therapeutic proteins after delivery of chemically modified mRNA in mice," Nature Biotechnology, vol. 29, No. 2, XP055040839, 2011, 6 Pages.
Benjamin Weide, et al. "Direct Injection of Protamine-protected mRNA: results of a Phase 1/2 Vaccination Trial in Metastatic Melanoma Patients," Journal of Immunother., vol. 32, No. 5, XP009154222, 2009, pp. 498-507.
Thierry Bettinger, et al. "Peptide-mediated RNA delivery: a novel approach for enhanced transfection of primary and post-mitotic cells," nucleic Acids Research, Vo. 29, No. 18. XP002374430, 2001, pp. 3882-3891.
Alan L. Parker, et al. "Targeting of Polyelectrolyte RNA Complexes to Cell Surface Integrins as an Efficient Cytopasmic Transfection Mechanism," Journal of Bioactive and Compatible Polymer, vol. 17, No. 4, XP009162825, 2002, pp. 229-238.
M. Mockey, el al. "mRNA-based cancer vaccine: prevention of B16 melanoma progression and metastasis by systemic injection of MART1 mRNA histidylated lipopolyplexes," Cancer Gene Therapy, vol. 14, No. 9, XP055007324, 2007, pp. 802-814.
Extended Search Report dated Dec. 6, 2017 in European Patent Application No. 14882238.0.
Satoshi Uchida, et al., "In Vivo Messenger RNA Introduction into the Central Nervous System Using Polyplex Nanomicelle", PLOS ONE, Public Library of Science, XP002729006, Feb. 2013, vol. 8, Issue 2, pp. e56220.1-e56220.8.
Naoki Kanayama, et al., "A PEG-Based Biocompatible Block Catiomer with High Buffering Capacity for the Construction of Polyplex Micelles Showing Efficient Gene Transfer toward Primary Cells", ChemMedChem, Apr. 2006, vol. 1, No. 4, pp. 439-444.
Kunwoo Lee, et al., "Peptide-enhances mRNA transfection in cultured mouse cardiac fibroblasts and direct reprogramming towards cardiomyocyte-like cells", International Journal of Nanomedicine, Mar. 2015, vol. 10, pp. 1841-1854.
Kanjiro Miyata, et al., "PEG-based block catiomers possessing DNA anchoring and endosomal escaping functions to form polyplex micelles with improved stability and high transfection efficacy", Journal of controlled release, vol. 122, No. 3, Sep. 2007, pp. 252-260.
Katalin Kariko, et al., "Increased Erythopoiesis in Mice Injected With Submicrogram Quantities of Pseudouridine-containing mRNA Encoding Erythropoietin", The America Society of Gene & Cell Therapy, XP002696191, vol. 20, No. 5, May 2012, pp. 948-953.
Database Embase, EMB 2010407547, Mar. 2010, XP002775460, 2 pages.
Database Biosis, Prev 200900216305, Jan. 2009, XP002775461, 2 pages.
Keith R. G. Martin, et al., "Gene Therapy with Brain-Derived Neutrotrophic Factor as a Protection: Retinal Ganglion Cells in a Rat Glaucoma Model", JOVIS, XP009158081; Oct. 2003, vol. 44, No. 10.
Hyun Jin Kim, et al., "Introduction of stearoyl moieties into a biocompatible cationic polyaspartamide derivative, PAsp(DET), with edosomal escaping function for enhanced siRNA-mediated gene knockdown", Journal of Controlled Release, vol. 145, No. 2, Jul. 2010, pp. 141-148.
Xin Geng; et al., "hepatitis B virus X Protein Targets the Bcl-2 protein CED-9 to induce Intracellular $Ca^{2+}$ increase and cell death in Caenorhabditis elegans" PNAS, Nov. 2012, vol. 109, No. 45, pp. 18465-18470.
Michiaki Kumagai, et al., "Effective transgene expression without toxicity by intraperitoneal administration of PEG-detachable polyplex micelles in mice with peritoneal dissemination", Journal of Controlled Release, vol. 160, No. 3, 2012, pp. 542-551.
Masahiro Ohgidani, et al., "Block/homo polyplex micelle-based GM-CSF gene therapy via intraperitoneal administration elicits antitumor immunity against peritoneal dissemination and exhibits safety potentials in mice and cynomolgus monkeys", Journal of Controlled Release, vol. 167, No. 3, Feb. 2013, pp. 238-247.
Lorrie A. Kirshenbaum, et al., "The BCI-2 Gene Product Prevents Programmed Cell Death of Ventricular Myocytes", American Heart Association, Sep. 1997, vol. 96, Issue 5, 21 pages.
Noah Weisleder, et al.. "Bcl-2, overexpression corrects mitochondrial defects and ameliorates inherited desmin null cardiomyopathy", PNAS, Jan. 2004, vol. 101, No. 3, pp. 769-774.
Nakanowatari F. et al., "Micelle formation from PEG-p(Lys) block copolymer with phenyl boronic acid moieties", Polymer Preprints, vol. 48, No. 3, The Journal of Society of Polymer Science, May 1999, XP008173084, 2 pages.
Japanese Office Action dated Sep. 4, 2018 in Japanese application No. 2015-562586.

* cited by examiner

FIG. 2A-1  FIG. 2A-2
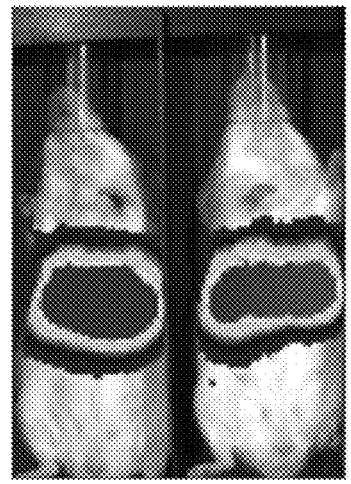 
mRNA INCLUSION MICELLE      BARE mRNA
FIG. 2B
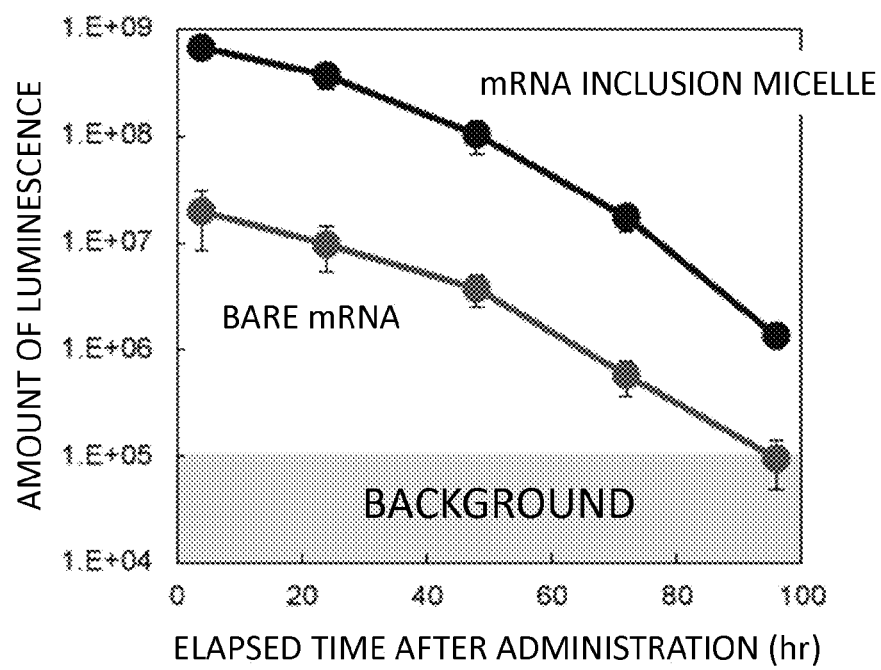

mRNA mRNA INCLUSION MICELLE pDNA

PLASMID DNA INCLUSION MICELLE

ELAPSED TIME AFTER ADMINISTRATION (hr)

OMP EXPRESSION

COMPOSITION FOR MRNA DELIVERY

TECHNICAL FIELD

The present invention relates to a polyion complex of mRNA and a polycationic polymer, and a composition and a pharmaceutical composition for mRNA delivery.

BACKGROUND ART

Drug delivery systems for delivering drugs to a suitable site in the body is researched and developed as providing new pharmaceutical agents having limited side effects. Among these systems, drug delivery systems using polyion complexes (hereinafter also referred to as "PIC") have attracted attention as techniques enabling drugs to be specifically delivered to affected parts by including the drugs in nanomicelles. The "polyion complex" generally means an ion layer obtained by mixing a copolymer of PEG and a cationic block and a copolymer of PEG and an anionic block in a solution, which ion layer is then formed between the cationic block and the anionic block, between the block copolymers. The linkage of the charged chain to PEG suppresses the aggregation and precipitation of the polyion complex and facilitates the formation of a nanoparticle having a monodisperse core-shell structure with a particle diameter of a few tens of nm. At that time, PEG covers the shell of the nanoparticle, which is known to be convenient in terms of increasing biocompatibility and enhancing blood residence time.

As techniques to which PIC is applied, systems have particularly been developed which can deliver nucleic acids into the body with limited side effects (Patent Literatures 1 and 2). Patent Literatures 1 and 2 propose polyion complexes of DNA and new cationic polymers.

CITATION LIST

Patent Literature

Patent Literature 1: Japanese Patent No. 4535229
Patent Literature 2: Japanese Patent No. 5061349

SUMMARY OF INVENTION

The present invention provides a composition and a pharmaceutical composition for mRNA delivery, and a polyion complex of mRNA and a polycationic polymer useful for these compositions.

The present inventors have found that a polyion complex of mRNA and a polycationic polymer can deliver mRNA into cells in the body of a subject almost without inducing inflammation. The present inventors have also found that the polyion complex can cause mRNA to be uniformly expressed in cells in the body of the subject. The present inventors have further found that the polyion complex causes mRNA to be rapidly expressed in cells in the body of the subject. Furthermore, the present inventors have found that the polyion complex causes mRNA to be sustainedly expressed in cells in the body of the subject. The present invention has been made based on the above findings.

Thus, according to the present invention, the following inventions are provided.

(1) A polyion complex comprising a cationic polymer and a messenger RNA (mRNA).

(2) The polyion complex according to (1) above, wherein the cationic polymer forms a block copolymer with a polyethylene glycol block.

(3) The polyion complex according to (1) or (2) above, wherein the cationic polymer is a polymer of monomeric units comprising:
a cationic natural amino acid,
a cationic non-natural amino acid, or
a cationic natural amino acid and a cationic non-natural amino acid.

(4) The polyion complex according to (3) above, wherein the cationic non-natural amino acid is an amino acid having a group represented by $-(NH-(CH_2)_2)_p-NH_2$ where p is an integer of 1 to 5 as a side chain.

(5) The polyion complex according to any one of (1) to (4) above, wherein the cationic polymer is a polycation block represented by general formula (I):

[Formula 1]

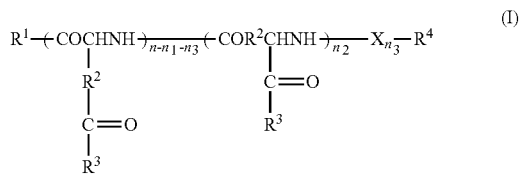

wherein
$R^1$ is a hydroxyl group, a protective group, or a polymerizable group;
$R^4$ is H, a protective group, a hydrophobic group, or a polymerizable group;
$R^2$ is methylene or ethylene;
$R^3$ is a group represented by $-(NH-(CH_2)_2)_p-NH_2$;
X is any one amino acid selected from cationic natural amino acids;
p is any integer of 1 to 5, and preferably, p is 2, 3, or 4;
n is any integer of 2 to 5,000;
$n_1$ is any integer of 0 to 5,000;
$n_3$ is any integer of 0 to 5,000;
$n-n_1-n_3$ is an integer of 0 or more,
although the repeating units in the formula are shown in the particular order for the purpose of description, the repeating units can be present in any order; the repeating units may be randomly present; and the repeating units may be the same or different, wherein when the polycation block forms a copolymer with polyethylene glycol, $R^1$ or $R^4$ represents a bond and polyethylene glycol forms a copolymer with the polycation block through $R^1$ or $R^4$ as the bond.

(6) The polyion complex according to (5) above, wherein the polycation block is a polycation block represented by general formula (II):

[Formula 2]

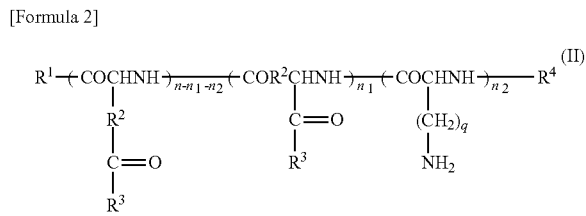

wherein
$R^1$ is a hydroxyl group, a protective group, or a polymerizable group;
$R^4$ is H, a protective group, a hydrophobic group, or a polymerizable group;

$R^2$ is methylene or ethylene;

$R^3$ is a group represented by —(NH—(CH$_2$)$_2$)$_p$—NH$_2$;

p is any integer of 1 to 5;

q is any integer of 1 to 5;

n is any integer of 2 to 5,000;

$n_1$ is any integer of 0 to 5,000;

$n_2$ is any integer of 0 to 5,000;

n-$n_1$-$n_2$ is an integer of 0 or more, although the repeating units in the formula are shown in the particular order for the purpose of description, the repeating units can be present in any order; the repeating units may be randomly present; and the repeating units may be the same or different, wherein when the polycation block forms a copolymer with polyethylene glycol, $R^1$ or $R^4$ represents a bond and polyethylene glycol forms a copolymer with the polycation block through $R^1$ or $R^4$ as the bond.

(7) The polyion complex according to any one of (1) to (6) above, wherein the mRNA is mRNA encoding a growth factor, a cell growth factor, a cytostatic factor, a cell death promoter, a cell death suppressor, a tumor-suppressor gene product, or a transcription factor.

(8) The polyion complex according to (7) above, wherein the cell growth factor is a hemopoietic factor or a brain-derived neurotrophic factor (BDNF).

(9) The polyion complex according to (7) above, wherein the cell death suppressor is Bcl-2.

(10) The polyion complex according to any one of (1) to (9) above, wherein the mRNA comprises modified cytidine and uridine.

(11) A method for delivering mRNA to the cytoplasm of a cell in the body of a subject, comprising administering the polyion complex according to any one of (1) to (10) above to a subject.

(12) The method according to (11) above for uniformly expressing a protein in a tissue of a subject or a portion thereof in the subject, comprising administering the polyion complex according to any one of (1) to (10) to the subject.

(13) The method according to (12) above, wherein the tissue is hepatic or mucosal tissue.

(14) A method for suppressing cell death in an affected area of an acute disease in a subject having the disease, comprising administering the polyion complex according to any one of (1) to (10) above to the subject, wherein the mRNA encodes a cell death suppressor.

(15) A method for promoting hemopoiesis in a subject in need thereof, comprising administering the polyion complex according to any one of (1) to (10) above to the subject, wherein the mRNA encodes a hemopoietic factor.

(16) A method for treating dysosmia in a subject having the dysosmia, comprising administering the polyion complex according to any one of (1) to (10) above to the subject, wherein the mRNA encodes a brain-derived neurotrophic factor (BDNF).

(17) A method for treating cancer in a subject having the cancer, comprising administering the polyion complex according to any one of (1) to (10) above to the subject, wherein the mRNA encodes a cytostatic factor, a tumor-suppressor gene product, or a cell death promoter.

(18) A composition for use in delivering mRNA into a cell in the body, comprising the polyion complex according to any one of (1) to (10) above.

(19) The composition according to (18) above, for use in uniformly expressing a protein in a tissue of a subject or a portion thereof in the subject.

(20) The composition according to (19) above, wherein the tissue is hepatic or mucosal tissue.

(21) A pharmaceutical composition comprising the polyion complex according to any one of (1) to (10) above.

(22) The pharmaceutical composition according to (21) above, for use in treating an acute disease in a subject in need thereof.

(23) The pharmaceutical composition according to (22) above, wherein the disease is fulminant hepatitis or acute spinal cord injury.

(24) The pharmaceutical composition according to (22) or (23) above, wherein the disease is a disease accompanied by stimulation of apoptosis.

(25) The pharmaceutical composition according to (21) above, for use in treating dysosmia in a subject in need thereof.

(26) The pharmaceutical composition according to (21) above for use in promoting hemopoiesis in a subject, wherein the mRNA encodes a hemopoietic factor.

The present invention, which enables the delivery of mRNA into a cell (particularly, cytoplasm), is advantageous in that the induction of inflammation is suppressed and a protein can be uniformly expressed early and throughout tissue.

BRIEF DESCRIPTION OF DRAWINGS

FIGS. 2A-1 and 2A-2 are a series of photographs when monitoring the expression of a protein by luciferase in mice to which mRNA inclusion micelles were administered through the tail vein by a hydrodynamics method. FIG. 2B is a graph showing a time-dependent change in the expression of the protein.

FIGS. 3A-1 and 3A-2 are photographs showing protein expression in a section of the liver of a mouse to which mRNA inclusion micelles were administered through the tail vein by a hydrodynamics method.

FIG. 6A shows the expression of the mRNA and its continuation in the mucosal epithelial cells of the nose. FIG. 6B shows the uniform expression of the mRNA throughout the entire mucosal epithelial tissue of the nose. FIG. 6C shows the therapeutic promotion effect of the mRNA inclusion micelles on dysosmia. FIG. 6D shows the photographs of sections of the mucosal epithelial tissue of the nose showing the therapeutic promotion effect of the mRNA inclusion micelles on dysosmia. FIG. 6E shows the expression of an olfactory marker protein (OMP) in the mucosal epithelial tissue of the nose at 28 days after treatment with the mRNA inclusion micelles.

DESCRIPTION OF EMBODIMENTS

Figure 1A:
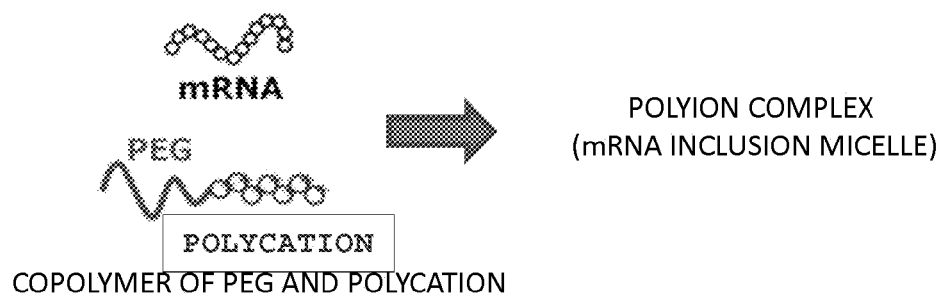
FIG. 1A is a schematic diagram showing the formation scheme of a polyion complex (mRNA inclusion micelle) using mRNA as an anionic polymer and using a block copolymer of PEG and a polycation as a cationic polymer.

The polyion complex of the present invention at least comprises (i) a block copolymer comprising a cationic polymer and (ii) mRNA. The cationic polymer may be one forming a block copolymer with a polyethylene glycol block. The copolymer of (i) and the mRNA of (ii) form a polyion complex in a solution. The polyion complex of the present invention can be provided in a solution, preferably in an aqueous solution.

As used herein, mRNA means messenger RNA.

In the polyion complex of the present invention, cytidine and uridine in the mRNA may be modified. Examples of the modified cytidine include 5-methyl-cytidine, and examples of the modified uridine include pseudouridine and 2-thio-cytidine. The modified forms of cytidine and uridine may be contained in an amount of 10% by mole or more, 20% by mole or more, or 30% by mole or more of the whole of cytidine and uridine.

The polyion complex of the present invention probably takes the form of a micelle including mRNA within the complex since it produces less inflammatory reaction attributed to the mRNA as shown in the examples to be stated later. Thus, the polyion complex is herein also referred to as "mRNA inclusion micelle". A micelle in which plasmid DNA is included in place of mRNA in the above mRNA inclusion micelle is herein referred to as "plasmid DNA inclusion micelle".

As used herein, the "micelle" means a vesicle formed by one layer of a molecular layer. Examples of the micelle include micelles formed by amphipathic molecules, such as a surfactant, and micelles formed by polyion complexes (PIC micelles). A micelle is known to be preferably modified in the outer surface with polyethylene glycol in view of blood retention time.

As used herein, the "subject" is a mammal including human. The subject may be a healthy subject or may be a subject suffering from some disease.

In the present invention, examples of the polycation block include a polymer block having a cationic natural amino acid and a cationic non-natural amino acid, for example, a cationic natural amino acid, such as histidine, tryptophan, ornithine, arginine, and lysine, and/or a group represented by —(NH—(CH$_2$)$_2$)$_p$—NH$_2$ (where p is an integer of 1 to 5) as side chains, for example, a polymer block of a cationic non-natural amino acid having the above cationic side chain, for example, a polymer block of a cationic non-natural amino acid, such as asparatic acid or glutamic acid having the above cationic side chain. In an embodiment of the present invention, the polycation block is a polymer block having a group represented by —(NH—(CH$_2$)$_2$)$_p$—NH$_2$ (where p is an integer of 1 to 5) as a side chain. Here, preferred examples of the cationic natural amino acid include histidine, tryptophan, ornithine, arginine, and lysine; more preferred examples thereof include arginine, ornithine, and lysine; and still more preferred example thereof include ornithine and lysine; and yet more preferred examples thereof include lysine.

In an embodiment of the present invention, the polycation block used is a polycation block represented by general formula (I):

[Formula 3]

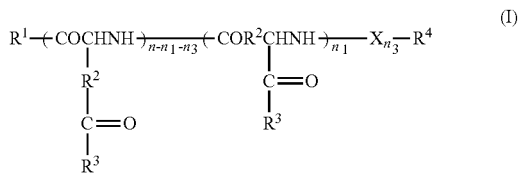

(wherein:

R$^1$ is a hydroxyl group, a protective group, or a polymerizable group;

R$^4$ is H, a protective group, a hydrophobic group, or a polymerizable group;

R$^2$ is methylene or ethylene;

R$^3$ is a group represented by —(NH—(CH$_2$)$_2$)$_p$—NH$_2$;

X is any one amino acid selected from cationic natural amino acids;

p is any integer of 1 to 5, and preferably, p is 2, 3, or 4;

n is any integer of 2 to 5,000, for example, any integer of 2 to 500;

n$_1$ is any integer of 0 to 5,000, for example, any integer of 0 to 500;

n$_3$ is any integer of 0 to 5,000, for example, any integer of 0 to 500;

n-n$_1$-n$_3$ is an integer of 0 or more, although the repeating units in the formula are shown in the particular order for the purpose of description, the repeating units can be present in any order; the repeating units may be randomly present; and the repeating units may be the same or different), wherein when the polycation block forms a copolymer with polyethylene glycol, R$^1$ or R$^4$ represents a bond and polyethylene glycol forms a copolymer with the polycation block through R$^1$ or R$^4$ as the bond.). In a polymer of the general formula (I), the repeating units bind to each other through a peptide bond.

The group represented by —(NH—(CH$_2$)$_2$)$_p$—NH$_2$ is known to induce the escape of the polyion complex from the endosome, and its characteristics are also known to vary depending on n. For this reason, a polymer block having groups represented by —(NH—(CH$_2$)$_2$)$_p$—NH$_2$ (where p is an integer of 1 to 5) as side chains can be preferably used in the present invention. In the present invention, the cationic side chain may be, for example, a group represented by —(NH—(CH$_2$)$_2$)$_p$—NH$_2$ (where p is 2 or 4), and this setting enables the protein expression in a cell to be induced early (for example, within 24 hours or within 12 hours). In the present invention, the cationic side chain may also be a group represented by —(NH—(CH$_2$)$_2$)$_p$—NH$_2$ (where p is 3), and this setting makes the release of mRNA from the polyion complex gentle and enables the long-term (e.g., 1 to 5 days) high protein expression.

In an embodiment of the present invention, amino acids form peptide bonds between their carboxyl groups and amino groups in the polymer of amino acids.

The polycation block may contain a cationic amino acid and an amino acid having a cationic side chain. Specifically, in an embodiment of the present invention, the polycation block is a polymer of a cationic natural amino acid, a cationic non-natural amino acid or units of a monomer comprising a cationic natural amino acid and a cationic non-natural amino acid. In an embodiment of the present invention, the bond between monomer units in the polycation block is a peptide bond. In a preferred embodiment of the present invention, the cationic non-natural amino acid is an amino acid having a group represented by —(NH—(CH$_2$)$_2$)$_p$—NH$_2$ (where n is an integer of 1 to 5) as a side chain. In an embodiment of the present invention, the polycation block may be a polycation block in which a cationic natural amino acid and asparatic acid and glutamic acid modified by a group represented by —(NH—(CH$_2$)$_2$)$_p$—NH$_2$ (where p is an integer of 1 to 5) are polymerized in any order. In an embodiment of the present invention, 40%, 50%, 60%, 70%, 80%, 90%, 95%, 98%, or 100% of monomer units in the polymer have a group represent by —(NH—(CH$_2$)$_2$)$_p$—NH$_2$ (where p is an integer of 1 to 5) as a side chain.

In an embodiment of the present invention, the polycation block comprises a polymer of one or more amino acids selected from lysine, asparatic acid, and glutamic acid as the main chain. In an embodiment of the present invention, in the main chain of the polycation block, one or more amino acids selected from lysine, asparatic acid, and glutamic acid account for 80%, 90%, 95%, or 98% of monomer units in the polymer. In an embodiment of the present invention, the main chain of the polycation block consists of a polymer of one or more amino acids selected from lysine, asparatic acid, and glutamic acid. In an embodiment of the present invention, substantially all of asparatic acid and glutamic acid residues each have a group represented by —(NH—(CH$_2$)$_2$)$_p$—NH$_2$ (where p is an integer of 1 to 5) as a side chain. In an embodiment of the present invention, the group represented by —(NH—(CH$_2$)$_2$)$_p$—NH$_2$ binds to the carboxylic acid group of asparatic acid or glutamic acid through a peptide bond In an embodiment of the present invention, the polycation block used is a polycation block represented by general formula (II) below:

[Formula 4]

$$R^1 + (COCHNH)_{n-n_1-n_2} + (COR^2CHNH)_{n_1} + (COCHNH)_{n_2} R^4 \atop \underset{\underset{R^3}{\overset{|}{C=O}}}{\overset{|}{R^2}} \quad \underset{R^3}{\overset{|}{C=O}} \quad \underset{NH_2}{\overset{|}{(CH_2)_q}}$$ (II)

(wherein:
R$^1$ is a hydroxyl group, a protective group, or a polymerizable group;
R$^4$ is H, a protective group, a hydrophobic group, or a polymerizable group;
R$^2$ is methylene or ethylene;
R$^3$ is a group represented by —(NH—(CH$_2$)$_2$)$_p$—NH$_2$;
p is any integer of 1 to 5, and preferably, p is 2, 3, or 4;
q is an integer of 1 to 5, preferably, q is 2, 3, or 4;
n is any integer of 2 to 5,000, for example, any integer of 2 to 500;
n$_1$ is any integer of 0 to 5,000, for example, any integer of 0 to 500;
n$_2$ is any integer of 0 to 5,000, for example, any integer of 0 to 500;
n-n$_1$-n$_2$ is an integer of 0 or more,
although the repeating units in the formula are shown in the particular order for the purpose of description, the repeating units can be present in any order; the repeating units may be randomly present; and the repeating units may be the same or different), wherein when the polycation block forms a copolymer with polyethylene glycol, R$^1$ or R$^4$ represents a bond and polyethylene glycol forms a copolymer with the polycation block through R$^1$ or R$^4$ as the bond.). In a polymer of the general formula (II), the repeating units bind to each other through a peptide bond.

In an embodiment of the present invention, the polyion block used is poly(Asp(diethyltriamine)) (hereinafter referred to as "poly(Asp(DET))"). The structure of poly(Asp (DET)) is represented by general formula (III) below. When the cationic polymer consists of a polycation block represented by the following general formula (III), R$_1$ and R$_4$ should not be a bond.
PolyAsp (DET)

[Formula 5]

$$R^1 + (COCHNH)_{n-m} + (COCHCH_2NH)_m R^4 \atop \underset{\underset{R^3}{\overset{|}{C=O}}}{\overset{|}{CH_2}} \quad \underset{R^3}{\overset{|}{C=O}}$$ (III)

(wherein:
R$^1$ is a hydroxyl group, a protective group, a hydrophobic group, or a polymerizable group;
R$^4$ is H, a protective group, a hydrophobic group, or a polymerizable group;
R$^3$ is a group represented by —(NH—(CH$_2$)$_2$)$_2$—NH$_2$;
n is any integer of 0 to 5,000, for example, any integer of 0 to 500;
m is any integer of 0 to 5,000, for example, any integer of 0 to 500;
m+n is any integer of 2 to 5,000, for example, any integer of 2 to 500;
n-m is an integer of 0 or more,
although the repeating units in the formula are shown in the particular order for the purpose of description, the repeating units can be present in any order; the repeating units may be randomly present; and the repeating units may be the same or different), wherein when the polycation block forms a copolymer with polyethylene glycol, R$^1$ or R$^4$ represents a bond and polyethylene glycol forms a copolymer with the polycation block through R$^1$ or R$^4$ as the bond.). In a polymer of the general formula (III), the repeating units bind to each other through a peptide bond.

In the general formulas (I), (II), and (III), examples of the protective group include C$_{1-6}$ alkylcarbonyl groups, preferably an acetyl group; examples of the hydrophobic groups include benzene, naphthalene, anthracene, pyrene, and derivatives thereof, or C$_{1-6}$ alkyl groups; and examples of the polymerizable group include a methacryloyl group and an acryloyl group. Methods for introducing the protective group, hydrophobic group, and polymerizable group into a block copolymer are well-known to those skilled in the art.

According to the present invention, regarding the cationic polymer, the polycation block may be linked to PEG. For example, compounds of the formulas (I), (II), and (III) may each form a block copolymer with polyethylene glycol through either R$^1$ or R$^4$ as a bond. The average polymerization degree of PEG is 5 to 20,000, preferably 10 to 5,000, more preferably 40 to 500; however, the degree is not particularly limited provided that the formation of a polyion complex of the block copolymer and mRNA is not inhibited.

Either $R^1$ or $R^4$ as a bond and PEG may bind to each other thorough a linker. The linker may be, for example, —$(CH_2)_r$—NH— (where r is an integer of 1 to 5) or —$(CH_2)_s$—CO— (where s is an integer of 1 to 5), and preferably binds to polycation blocks of the formulas (I), (II), and (III) through a peptide bond. The linker also preferably binds to PEG in the side of methylene through the O atom of PEG. The carbon atom in another terminal of PEG may be substituted by a hydroxyl group, a methoxy group, or a protective group.

In other words, in an embodiment of the present invention, the block copolymer of a PEG-linker-polycation block is used as a cationic polymer (where PEG, the linker, and the polycation block are as defined above).

The present inventors previously reported a micelle including plasmid DNA (WO2006/085664). WO2006/085664 discloses a technique for including less immunogenic DNA in a micelle. Specifically, WO2006/085664 discloses that the pDNA inclusion micelle formed by the cationic polymer and plasmid DNA using polyAsp (DET) or a block copolymer of PEG and polyAsp (DET) as a cationic polymer is less toxic in vivo and causes a gene in the plasmid DNA to be efficiently expressed. WO2006/085664 discloses that in the process of being incorporated into a cell, the micelle extremely efficiently escapes from the endosome into the cytoplasm when $R^3$ is a group represented by —(NH—$(CH_2)_2)_2$—$NH_2$ in the general formulas (I) and (II).

Unlike less immunogenic DNA, mRNA is familiar from extremely high immunogenicity, and it was probable that to deliver mRNA into the cytoplasm without inflammation, it was necessary to continue to completely encapsulate the mRNA in a micelle in the whole process until it was delivered into the cytoplasm. Thus, the introduction of mRNA into the body was expected to be difficult even when it was included in a micelle. However, according to the present inventors, the mRNA inclusion micelle of the present invention, surprisingly, has caused little inflammatory reaction in the body. This suggests that the mRNA inclusion micelle of the present invention can specifically deliver mRNA into the cytoplasm.

The mRNA inclusion micelle of the present invention has caused the uniform protein expression in almost 100% of cells in the liver in vivo (FIGS. 3A-1 and 3A-2), while the pDNA inclusion micelle has resulted in the expression of DNA only in a part of the cells. This indicates that the mRNA inclusion micelle of the present invention can be highly advantageously used when mRNA is desired to be uniformly expressed throughout tissue. The mRNA inclusion micelle of the present invention highly quickly caused the expression of the protein encoded by the mRNA in vivo. Thus, the mRNA inclusion micelle of the present invention can be advantageously used when the rapid expression of protein is demanded.

Thus, according to the present invention, there is provided a composition for delivering mRNA into the cytoplasm in the body of a subject, comprising a polyion complex of a cationic polymer and the mRNA. In other words, the composition of the present invention is a mRNA-delivering agent for delivering mRNA into the cytoplasm in the body of a subject.

As just described, the polyion complex of the present invention enables the uniform expression of mRNA in a wide range of cells, enables the rapid expression of mRNA after administration, and/or hardly causes inflammatory reaction in the body. Thus, the polyion complex of the present invention can be preferably used in the treatment of diseases requiring the expression of mRNA in a wide range of cells and requiring the rapid expression of mRNA, for example, a disease whose condition rapidly progresses and an acute disease.

Thus, according to the present invention, there is provided a composition for use in delivering mRNA into the body of a subject having a disease whose condition rapidly progresses or an acute disease, comprising the polyion complex of the present invention. According to the present invention, there is provided a pharmaceutical composition for use in treating a disease whose condition rapidly progresses or an acute disease, comprising the polyion complex of the present invention.

In diseases involving rapid death of cells, cell death-suppressing treatment can prevent the progression or worsening of symptoms. The polyion complex of the present invention can be advantageously used in the treatment of such diseases on condition that mRNA is a cell death-suppressing factor. In diseases involving rapid apoptosis of cells, apoptosis-suppressing treatment can prevent the progression or worsening of symptoms. The polyion complex of the present invention can be advantageously used in the treatment of such diseases on condition that mRNA is an anti-apoptosis factor. Examples of the disease involving rapid cell death or apoptosis include acute spinal cord injury and fulminant hepatitis.

In acute spinal cord injury and fulminant hepatitis, cell death (apoptosis) occurs in a wide range of cells of an affected area. Specifically, acute spinal cord injury results in the death of many nerve cells in the injured area. In fulminant hepatitis, the death of a wide range of hepatic cells occurs in the liver, resulting in the induction of hepatic failure. In acute spinal cord injury and fulminant hepatitis, symptoms are prevented from worsening or improved by performing treatment for uniformly suppressing cell death throughout tissue. Consequently, the pharmaceutical composition of the present invention capable of causing the uniform expression of a protein throughout tissue can be preferably used for the treatment of these diseases.

Thus, in an embodiment, the pharmaceutical composition of the present invention is one suppressing cell death, and comprises, for example, mRNA encoding a cell death-suppressing factor. In an embodiment, the pharmaceutical composition of the present invention is one suppressing apoptosis, and comprises, for example, mRNA encoding an anti-apoptosis factor.

The anti-apoptosis factor is not particularly limited; however, examples thereof include FLIP, Mcl-1, Xiap, crmA, Bcl-2, and Bcl-xL and Bcl-2 can be preferably used. As just described, when the acute disease is a disease involving the stimulation of cell apoptosis, particularly an acute disease, the mRNA is mRNA encoding an anti-apoptosis factor.

The polyion complex of the present invention, which can efficiently deliver mRNA into cells, can also be applied to the treatment of various other diseases. Examples of the mRNA used in the present invention include mRNAs encoding a growth factor, a cell growth factor, a cytostatic factor, a cell death promoter, a cell death suppressor, a tumor suppressor gene product, and a transcription factor; it will be properly selected according to the particular purpose by those skilled in the art. For example, mRNA encoding a growth factor for a particular cell can be administered as a polyion complex to a subject requiring the growth of the particular cell to treat a disease or a condition in the subject.

The growth factor means an endogenous protein promoting the growth or differentiation of a particular cell and is not particularly limited; however, examples thereof include epidermal growth factor (EGF), insulin-like growth factor (IGF), nerve growth factor (NGF), brain-derived neurotrophic factor (BDNF), vascular endothelial cell growth factor (VEGF), granulocyte colony-stimulating factor (G-CSF), granulocyte-macrophage colony-stimulating factor (GM-CSF), platelet-derived growth factor (PDGF), erythropoietin (EPO), thrombopoietin (TPO), basic fibroblast growth factor (bFGF or FGF-2), and hepatocyte growth factor (HGF). The cytostatic factor is not particularly limited; however, examples thereof include p21, p17, p16, and p53. The cell death promoter is not particularly limited; however, examples thereof include Smac/Diablo, apoptosis-inducing factor (AIF), HtrA2, Bad, Bim, Bax, p53, caspases 1, 2, 3, 4, 5, 6, 7, 8, 9, and 10 (for example, caspases 2, 3, 6, 7, 8, 9, and 10, preferably caspases 3, 6, and 7), Fas ligand (Fas L), tumor necrosis factor-related apoptosis inducing ligand (TRAIL), and FoxO1. Examples of the cell death suppressor include anti-apoptosis factors as described above. The tumor suppressor gene product is not particularly limited; however, examples thereof include p53, retinoblastoma gene (Rb), adenomatous polyposis coli gene (APC), neurofibromatosis type 1 gene (NF1), neurofibromatosis type 2 gene (NF2), WT1, VHL, BRCA1, BRCA2, CHEK2, Maspin, p73, Smad4, MSH2, MLH1, PMS2, DCC, phosphatase and tensin homolog (PTEN), SDHD, p16, p57$^{Kip2}$, PTC, TSC1, TSC2, EXT1, and EXT2. The transcription factor is not particularly limited; however, examples thereof include Runt-related transcription factor 1 (Runx1), p53, c-fos, c-Jun, CREB, C/EBP, MyoD, c-Myc, c-Myb, Oct3/4, Nf-κB, NF-AT, Mef-2, and extracellular signal response factor (SRF).

According to the present invention, there is provided, for example, a pharmaceutical composition for use in promoting hemopoiesis in a subject in need of promotion of hemopoiesis (for example, an anemia patient), comprising the polyion complex of the present invention in which the mRNA encodes hemopoietic factor (for example, colony-stimulating factor or erythropoietin).

According to the present invention, there is provided, for example, a pharmaceutical composition for use in treating dysosmia in a subject having dysosmia involving a disruption of olfactory tissue (for example, mucosal epithelial cells or olfactory nerve), comprising the polyion complex of the present invention in which the mRNA encodes brain-derived neurotrophic factor (BDNF).

In another aspect of the present invention, there is provided a pharmaceutical composition for use in treating cancer in a subject having the cancer, comprising the polyion complex of the present invention, wherein the mRNA encodes a cytostatic factor, a tumor suppressor gene product, or a cell death promoter. For cancer tissue, it is desired to suppress the growth of all cancer cells; thus, the pharmaceutical composition of the present invention enabling the uniform expression of a growth-suppressive factor throughout the cancer tissue can be particularly suitably used. In the pharmaceutical composition for use in treating cancer, the polyion complex of the present invention preferably has a particle diameter of 20 to 100 nm. This facilitates the entry of the polyion complex of the present invention into cancer tissue through capillary blood vessels around the tissue.

The pharmaceutical composition of the present invention may further comprise an excipient.

In an aspect of the present invention, there is provided a method for delivering mRNA to the cytoplasm of a cell in the body of a subject, comprising administering the polyion complex of the present invention to the subject.

In an aspect of the present invention, there is provided a method for delivering mRNA to the cytoplasm of a cell in the body of a subject which is used for uniformly expressing a protein in tissue or a part thereof in the subject, comprising administering the polyion complex of the present invention to the subject, wherein the mRNA encodes a protein desired to be expressed. In an embodiment, the tissue is liver or mucosal tissue (for example, olfactory epithelium tissue).

Although the polyion complex can be delivered to an organ (for example, liver) by intravenous injection, the hydrodynamics method can markedly enhance the efficiency of delivery of the polyion complex to an organ (for example, liver). The hydrodynamics method is a method for administering about the same amount of a drug solution as the amount of blood through a vein in a short time, which involves permeating the inside of an organ with the drug solution by pressure in administration. A hydrodynamics method is known for which the area is limited; for example, a method is also known which involves temporarily stopping blood flow around a target area and administering to the target area about the same amount of a drug solution as the amount of the blood contained in the area to permeate the target tissue with the drug solution, and this method can be used in the present invention.

The polyion complex of the present invention can be delivered to mucosal tissue by the application thereof. The PIC of the present invention permeates into the depth of the mucosal tissue by application and is incorporated into the tissue or a part thereof.

Those skilled in the art can select a suitable administration method to deliver the polyion complex to various tissues. Examples of the administration method used in the present invention include subcutaneous injection, intramuscular injection, intraarticular injection, and subarachnoid cavity injection. A method is known which involves leaving the polyion complex in a place beneath a subcutis or muscular layer by infiltration into a carrier, such as a collagen sponge, for the slow release of the polyion complex, and this method can be used in the present invention.

In another aspect, there is provided a method for suppressing cell death in an affected area of an acute disease in a subject having the disease, comprising administering the polyion complex of the present invention in which the mRNA encodes a cell death suppressor to a subject. In an embodiment of the present invention, the cell death is apoptosis, and the cell death suppressor is an anti-apoptosis factor.

In another aspect of the present invention, there is provided a method for suppressing cell death in a subject having a disease involving the stimulation of the cell death, comprising administering the polyion complex of the present invention in which the mRNA encodes a cell death suppressor to a subject. In an embodiment of the present invention, the cell death is apoptosis, and the cell death suppressor is an anti-apoptosis factor.

In another aspect of the present invention, there is provided a method for treating fulminant hepatitis or acute spinal cord injury, comprising administering the polyion complex of the present invention to the subject, wherein the mRNA encodes a cell death suppressor. In an embodiment of the present invention, the cell death suppressor is an anti-apoptosis factor.

In another aspect of the present invention, there is provided a method for promoting hemopoiesis in a subject in need of promotion of hemopoiesis (for example, an anemia patient), comprising administering the polyion complex of the present invention to the subject, wherein the mRNA encodes hemopoietic factor (for example, colony-stimulating factor or erythropoietin).

In another aspect of the present invention, there is provided a method for treating dysosmia in a subject having dysosmia involving a disruption of olfactory tissue (for example, mucosal epithelial cells or olfactory nerve), comprising administering the polyion complex of the present invention to the subject, wherein the mRNA encodes brain-derived neurotrophic factor (BDNF).

In still another aspect of the present invention, there is provided a method for treating cancer in a subject having the cancer, comprising administering the polyion complex of the present invention to the subject, wherein the mRNA encodes a cytostatic factor, a tumor suppressor gene product, or a cell death promoter.

EXAMPLES

Example 1: Preparation of Polyion Complex

A polyion complex containing mRNA was first prepared.
A block copolymer of polyethylene glycol (PEG) and a polycation was used as a block copolymer capable of forming a polyion complex with mRNA having a negative charge (FIG. 1A).

The PEG-polycation block copolymer used was a PEG-pAsp(DET) block copolymer.

1-1. Synthesis of PEG-pAsp(DET) Block Copolymer

The PEG-pAsp(DET) block copolymer was first synthesized. Specifically, polyethylene glycol with a number average molecular weight of 12,000, having a methoxy group at one end and an aminopropyl group at the other end (MeO-PEG-NH$_2$) was dissolved in methylene chloride. β-Benzyl-L-aspartate-N-carboxylic anhydride (BLA-NCA) (produced by commission to Chuo Kaseihin Co., Inc.) was dissolved in a mixed solution of N,N-dimethylformamide (DMF) and the methylene chloride solution to provide a reaction solution. Then, the reaction solution was reacted at 40° C. for two days to provide polyethylene glycol-poly(β-benzyl-L-aspartate) block copolymer (MeO-PEG-PBLA).

The amino end of MeO-PEG-PBLA was reacted with acetic anhydride for acetylation to provide MeO-PEG-PBLA-Ac. Analysis by $^1$H-NMR showed that the PBLA moiety had a number average molecular weight of 14,000 and a polymerization degree of 70.

Then, MeO-PEG-PBLA-Ac was reacted with diethylenetriamine to provide MeO-PEG-pAsp(DET) block copolymer. Specifically, MeO-PEG-PBLA-Ac was dissolved in benzene and freeze-dried. The freeze-dried MeO-PEG-PBLA-Ac was dissolved in N-methyl-2-pyrrolidone (NMP). Thereafter, the resultant solution was drop-wise added to an NMP solution of diethylenetriamine and stirred at 5 to 10° C. for one hour. The resultant was further neutralized with hydrochloric acid under cooling with ice, dialyzed, and freeze-dried to provide MeO-PEG-pAsp(DET) block copolymer. The dialysis was performed using a 0.01 N hydrochloric acid aqueous solution as an external dialysate and finally using pure water at 4° C. Analysis by $^1$H-NMR showed that the pAsp(DET) moiety of the resultant MeO-PEG-pAsp(DET) block copolymer had a polymerization degree of 63.

1-2. Preparation of mRNA mRNA was prepared by performing in vitro transcription using mMESSAGE mMACHINE T7 Ultra Kit (Ambion, Invitrogen, Carlsbad, Calif., USA) and using plasmid DNA as a template. The plasmid DNA was first prepared by introducing luciferase gene, GFP gene, erythropoietin gene, or Bcl-2 gene under control of T7 promoter and incorporating 120-base poly A sequence downstream of each gene. Modified mRNA was obtained by adding 5-methyl-CTP, pseudo-UTP, and 2-thio-UTP (TriLink BioTechnologies, San Diego, Calif., USA) as bases in in vitro transcription. Specifically, in the in vitro transcription, 20% by mole of 5-methyl-CTP based on the total CTP and 10% each of pseudo-UTP and 2-thio-UTP based on the total UTP were added. The non-modified mRNA and modified RNA obtained by transcription were purified using RNeasy Mini Preparation Kit (Qiagen, Hilden, Germany). The mRNA concentration was measured using absorbance at 260 nm.

1-3. Preparation of Polyion Complex

A PEG-pAsp(DET) solution (10 mM Hepes (pH 7.3)) and a mRNA solution (10 mM Hepes (pH 7.3)) or a plasmid DNA solution (10 mM Hepes (pH 7.3)) were mixed to provide a polyion complex (referred to as mRNA inclusion micelle or plasmid DNA inclusion micelle, respectively). The mixing was performed so that the mixing ratio of the amino groups (N) of amino acid residues in PEG-pAsp (DET) to phosphate groups in the nucleic acid (N/P) is 3. The final nucleic acid concentration was adjusted to 33.3 mg/mL. The particle diameter of the resultant micelle was measured by dynamic light scattering (DLS). The resultant mRNA inclusion micelle had a particle diameter of about 50 nm, and the resultant plasmid DNA inclusion micelle had a particle diameter of about 90 nm.

Example 2: Test of Administration of mRNA Inclusion Micelle

In this Example, the micelles obtained in Example 1 were administered to experimental animals to examine the expression of a protein from mRNA.

The experimental animal used was Balb/c (female, seven weeks old) purchased from Charles River Laboratories Japan, Inc. The mRNA inclusion micelles were administered to the mouse by a hydrodynamics method. Specifically, 5 μg of the mRNA inclusion micelles or the plasmid DNA inclusion micelles were diluted in 1.8 mL of physiological saline and the total amount thereof was administered through the tail vein of the mouse for five seconds. The agent administered by the hydrodynamics method is known to be efficiently incorporated into hepatic cells.

Gaussia luciferase (GLuc) was used as a secretory protein. The mRNA inclusion micelles or the GLuc protein was administered into the cervical subarachnoid cavity, and the protein amount in the spinal fluid after administration was monitored for five days.

Figure 1B:
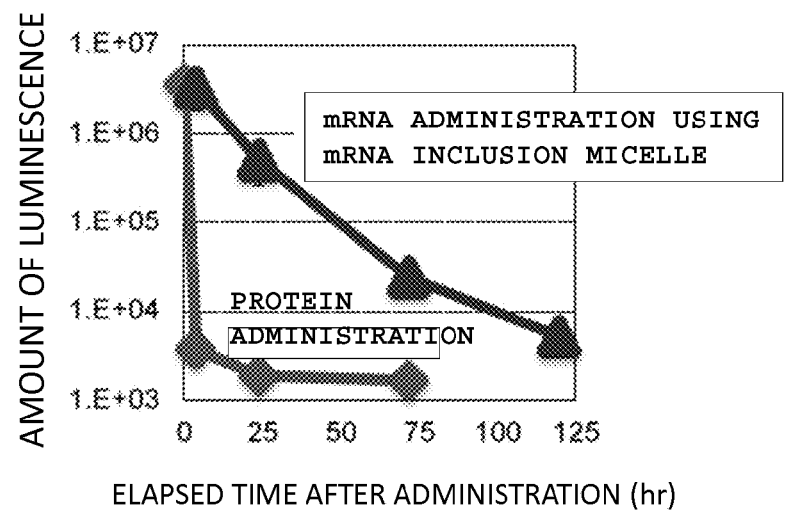
FIG. 1B is a graph showing the expression of a protein in the spinal fluid of mice to which mRNA inclusion micelles were administered through the cervical subarachnoid space.

As a result, as shown in FIG. 1B, when mRNA was administered using the mRNA inclusion micelles, the sustained expression of GLuc was observed.

Example 3: Delivery of mRNA to Liver

The mRNA inclusion micelles were administered to mice by the same method as in Example 2, and the accumulation of mRNA in the liver and its expression were monitored.

3-1. Expression of Protein in Liver

The expression of a protein in the liver was quantified by luminescence of luciferase. Specifically, D-luciferin (Sumitomo Pharma) (150 mg/kg) was intraperitoneally administered to mice to which the micelles including mRNA capable of expressing luciferase or bare mRNA had been administered, four hours after administration, and its luminescence was observed and quantified using IVIS Imaging System (Xenogen, Alameda, Calif., USA).

Figures 1, 3A:
Figures 2, 3A:
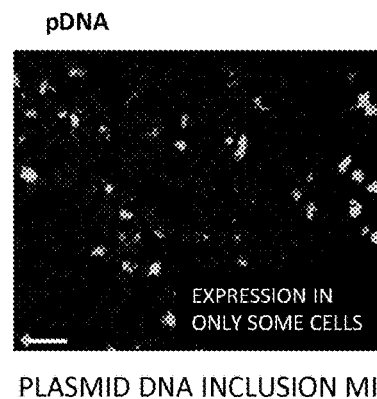

As a result, as shown in FIGS. 2A-1, 2A-2 and 2B, the strong luminescence of luciferase was observed in mice to which the mRNA inclusion micelles were administered, while only weak luminescence was observed in mice to which bare mRNA was administered. The luminescence of luciferase was also maintained for longer periods of time in mice to which the mRNA inclusion micelles were administered (FIG. 2B).

3-2. Immunohistological Analysis of Protein Expression in Liver

In addition, the protein expression in the liver was immunohistologically monitored in detail. For this purpose, the liver was harvested from mice to which were administered micelles including mRNA or plasmid DNA capable of expressing GFP, 24 hours after administration. The resultant liver was fixed in a phosphate buffer solution containing 4% paraformaldehyde (Wako Pure Chemical Industries Ltd.) overnight and then allowed to stand at ordinary temperature in PBS solutions containing 10%, 15%, and 20% sucrose for four hours, four hours, and overnight, respectively, followed by freeze-drying in an optical cutting temperature (OCT) compound (Sakura Finetek, Torrance, Calif., USA). Thereafter, tissue sections 10 µm in thickness were prepared. For the immunostaining of GFP, the sections were each reacted with a 1/500 dilution of anti-GFP rabbit IgG (Invitrogen) as a primary antibody at room temperature overnight and then reacted with a 1/200 dilution of Alexa 488 goat anti-rabbit IgG (Invitrogen) as a secondary antibody at room temperature for 1 hour. The antibody-stained section was observed using In Cell Analyzer 1000 (GE Healthcare, Buckinghamshire, UK), which was a fluorescence microscope equipped with an image analysis function.

Figure 3B:
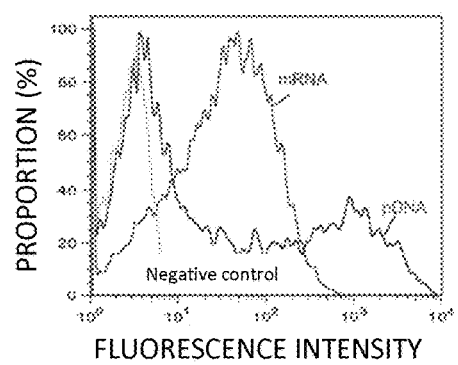
FIG. 3B is a graph showing the results of analysis of its image.

As a result, as shown in FIGS. 3A-1 and 3A-2, all cells uniformly expressed GFP protein in the liver of the mouse to which the mRNA inclusion micelles were administered; however, for the plasmid DNA inclusion micelles, some cells exhibited strong expression of GFP protein while many cells were not observed to express GFP protein. This was also supported from the results of the distribution of fluorescence intensity (FIG. 3B).

3-3. Degradation of Administered mRNA Amount in Liver

To confirm the presence of degradation of mRNA in the liver, the amount of the administered mRNA was quantified by both a method using a fluorescence-labeled nucleic acid and a quantitative PCR method. In the quantitative PCR, the amount of mRNA whose full-length sequence is maintained is quantified, and in the method using a fluorescence-labeled nucleic acid, all mRNAs including degraded mRNAs are quantified. By the method of Example 2, mRNA inclusion micelles or bare mRNA was administered to mice and the liver was harvested after 10 minutes and quantified for the mRNA.

The method using a fluorescence-labeled nucleic acid was performed as follows. The liver was harvested and homogenized after introducing mRNA Cy5-labeled using Label IT™ Nucleic Acid Labeling Kit, Cy5 (Mirus, Madison, Wis., USA) by including or not including in the micelles. Thereafter, the amount of fluorescence in the homogenized solution was measured on a fluorescence plate reader (TECAN, Mannedorf, Switzerland).

The quantitative PCR method was performed as follows. After introducing mRNA capable of expressing luciferase by including or not including in micelles, the mRNA was extracted from the harvested liver using RNA easy mini preparation kit (Qiagen). In the quantitative PCR, the primer set of TGCAAAAGATCCTCAACGTG and AATGGGAAGTCACGAAGGTG was used, and detection was performed using ABI Prism 7500 Sequence Detector (Applied Biosystems, Foster City, Calif., USA). In both methods, the amount of mRNA introduced into the liver was determined from the proportion (%) of the amount of mRNA introduced into the liver in the amount of administered mRNA.

Figure 3C:
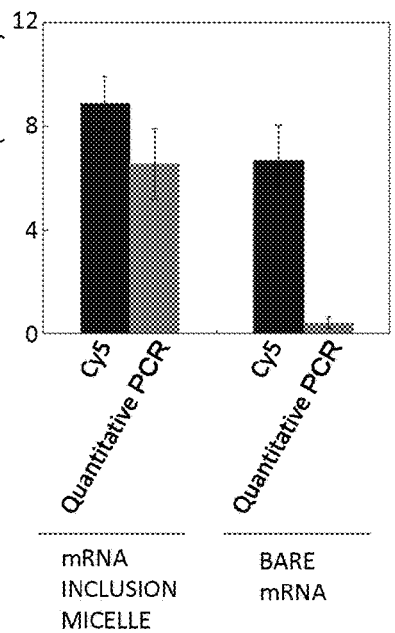
FIG. 3C is a graph showing the reduced decomposition of mRNA delivered by the mRNA inclusion micelles in the liver.

As a result, mRNA was rapidly degraded in the liver in mice to which the bare mRNA was administered, whereas the degradation of mRNA was rarely observed in mice to which the mRNA inclusion micelles were administered (FIG. 3C).

Example 4: Inflammatory Reaction by mRNA Inclusion Micelle

In this Example, inflammatory reaction was examined which occurred by introducing mRNA inclusion micelles.

The induction of inflammation by introducing mRNA was evaluated. Specifically, mRNA inclusion micelles were administered to mice as described in Example 2. mRNA extracted four hours after administration according to the method of Example 3-3 was used to quantify the amount of inflammatory cytokine mRNA by quantitative PCR using ABI Prism 7500 Sequence Detector (Applied Biosystems) and Taqman Gene Expression Assays (Applied Biosystem, IL-6: Mm00446190_m1, TNF-α: Mm00443258, IFN-β: Mm00439552 s1). The mRNA amount was standardized with the mRNA amount for the β-actin amount (Mm00607939). Mice to which physiological saline was administered were used as a control.

Figure 4A:
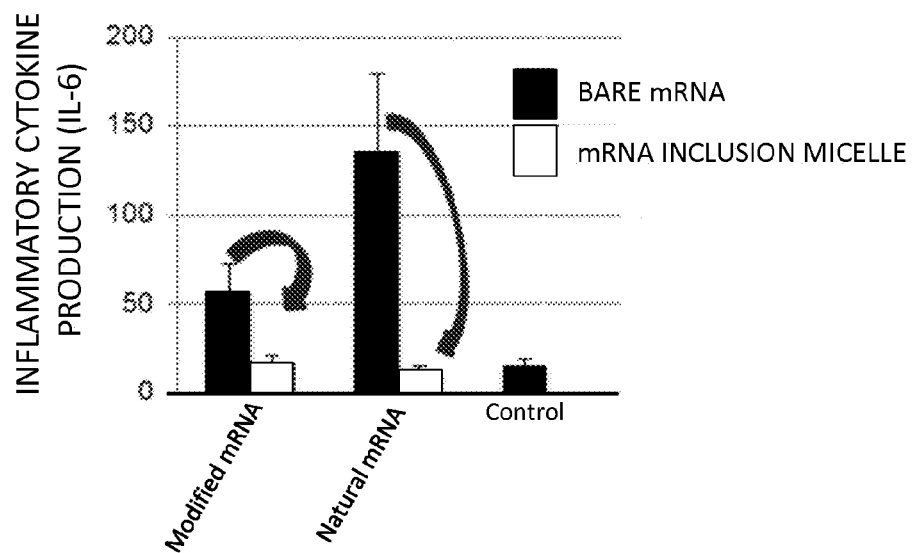
FIG. 4A is a graph showing a reduction in the inflammation induced in mice to which mRNA inclusion micelles were administered.

As a result, the production amount of the inflammatory cytokine IL-6 was extremely low for non-modified mRNA (natural) inclusion micelles compared to when bare mRNA was introduced (FIG. 4A). Modified mRNA resulted in the low production amount of the inflammatory cytokine IL-6 compared to when non-modified mRNA was introduced, but its inclusion in micelles could lead to a reduction in the production amount of the inflammatory cytokine IL-6 (FIG. 4A). Since mRNA is known for its strong immunogenicity, it was surprising that the production of the inflammatory cytokine was comparable to that in the control mice.

The mRNA inclusion micelle is probably incorporated into a cell by endocytosis. Since pH is low inside the endosome, the mRNA inclusion micelle probably changes in the amine structure of the side chain to increase its fusogenicity, and thereby transfers from the endosome into a cell (Miyata et al., J. Am. Chem. Soc., 130 (48): 16287-16294 (2008)). Toll-like receptors (TLR) are expressed on the inner surface of the endosome, and elicit natural immunity when recognizing mRNA. Thus, the release of mRNA within the endosome elicits strong innate immune reaction even if it is a small amount. However, surprisingly, the mRNA inclusion micelle of the present invention hardly elicited inflammatory reaction.

From these results, it will be seen that the micelle of the present invention is a micelle including mRNA and that the micelle has high selectivity enabling the delivery of the mRNA into the cytoplasm without release in the endosome. This surprising property of the mRNA inclusion micelle of the present invention also probably enabled the efficient delivery of mRNA into a cell.

The duration of the protein expression was also compared between a non-modified mRNA inclusion micelle and a modified RNA inclusion micelle. The mRNA of luciferase was used as mRNA, and the expression level of luciferase was measured by the method described in Example 3.

Figure 4B:
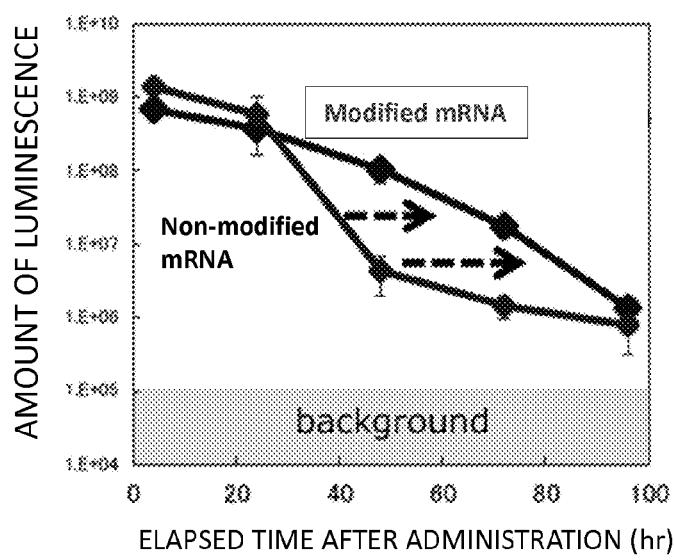
FIG. 4B is a graph showing that modified RNA can result in the prolonged duration of the protein expression.

As a result, more sustained expression was shown for the modified mRNA inclusion micelle (FIG. 4B).

Example 5: Hemopoiesis Recovery Experiment

In this Example, hemopoiesis recovery in mice to which micelles including mRNA for erythropoietin were administered was confirmed.

Blood was collected from mice to which micelles including the mRNA of erythropoietin gene were administered by the method described in Example 2, 28 days or 56 days after administration to measure hematocrit and hemoglobin levels using pocH-100i (Sysmex Corporation, Hyogo).

Figure 5A:
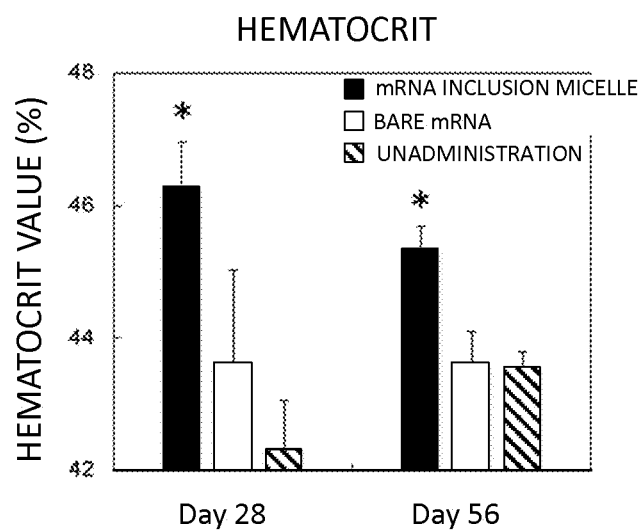
FIGS. 5A and 5B are a pair of graphs showing the recovery of hemopoiesis in mice to which mRNA inclusion micelles in which mRNA encoding erythropoietin was included as a mRNA were administered.
Figure 5B:
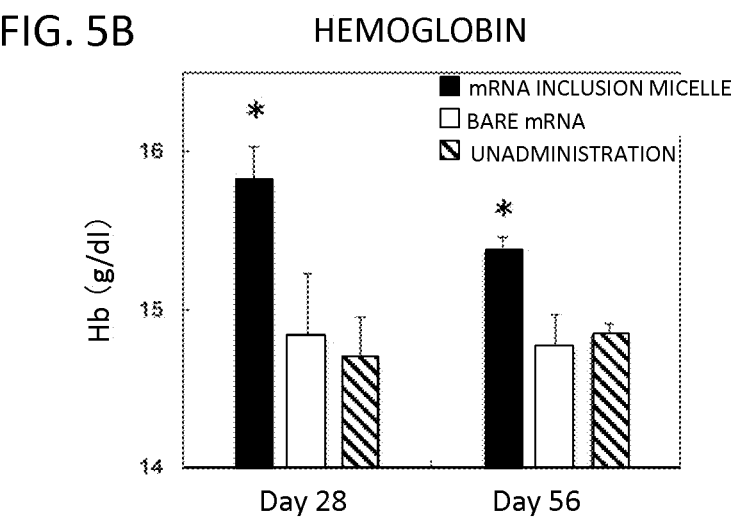

As a result, both of the hematocrit and hemoglobin levels exhibited significant increases in the mice to which the mRNA inclusion micelles were administered, showing that the micelles have an effective and sustained hemopoietic effect (FIGS. 5A and 5B).

Example 6: Therapy of Dysosmia Model Animal by Nasal Drip

In this Example, the therapy of dysosmia model animals by the nasal drip of mRNA inclusion micelles was attempted.

6-1. Quantification of Expression of Luciferase Protein

The micelles including mRNA encoding luciferase were first prepared by the method described in Example 1 except for setting the final nucleic acid concentration to 200 μg/mL. Four mice were retained in the supine position under anesthesia to drip 50 μL of a solution of the mRNA inclusion micelles (containing 10 μg of the mRNA) on the nostril. As a control, 10 μg of bare plasmid DNA (pDNA) or mRNA not included in micelles was dripped on the nostril. Four, 24, and 48 hours after administration, 200 μL of 15 mg/mL D-luciferin (Sumitomo Pharma) was subjected to nasal drip. Ten minutes thereafter, luciferase luminescence was observed and quantified using IVIS Imaging System (Xenogen, Alameda, Calif., USA).

Figure 6A:
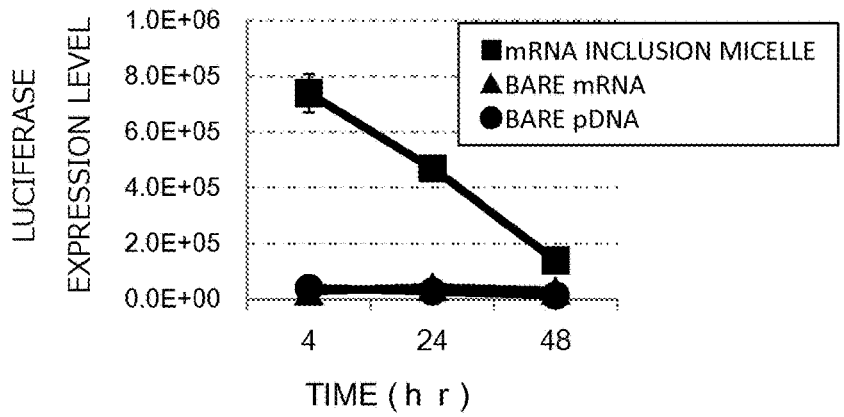
FIGS. 6A-6E show the effect of the expression of a brain-derived neurotrophic factor (BDNF) using mRNA inclusion micelles in dysosmia model mice.

As a result, as shown in FIG. 6A, the high expression of luciferase was observed for the mRNA inclusion micelle. The expression was observed from four hours after the micelle administration and sustained for 48 hours thereafter.

It was very unexpected that the transfection of cultured cells with mRNA resulted in the sustainment of its expression for 48 hours for the present invention, because it typically resulted in the sustainment of its expression for at longest only about 48 hours from several hours after the transfection.

The same experiment was also performed using micelles including luciferase expression plasmid DNA in place of the mRNA; however, no protein expression was observed (data presentation was omitted). The administration of bare mRNA or DNA encoding luciferase also resulted in no observation of protein expression (data omitted).

6-2. Quantification of Expression of GFP Protein (Immunohistochemistry)

The micelles including mRNA encoding GFP were prepared by the same method as the method for preparing the luciferase mRNA inclusion micelle of the Example. A solution of the mRNA inclusion micelle (50 μL) (containing 10 μg of the mRNA) was dripped on the nostril. Twenty four hours after administration, mice were euthanized to excise the nasal part, and frozen sections 5 μm in thickness were prepared from the anterior border of the olfactory bulb.

The immunohistochemical staining of the expressed GFP protein was carried out according to an ordinary method. A 1/500 dilution of anti-GFP rabbit IgG (from Invitrogen) was used as a primary antibody and reacted with the sections at room temperature overnight. A 1/200 dilution of Alexa 488 goat anti-rabbit IgG (from Invitrogen) was used as a secondary antibody and reacted with the sections at room temperature for one hour. The nucleus was stained with a blocking solution containing Hoechst 33342 (Dojindo, Kumamoto, Japan). The resultant sections were observed using a fluorescence microscope (Axiovert 200 fluorescence microscope (Carl Zeiss, Jena, Germany)) as a microscope and 20×EC Plan Neofuar objective (Carl Zeiss) as an object lens.

Figure 6B:
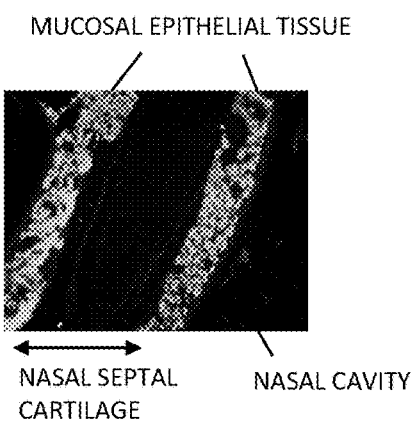

As a result, as shown in FIG. 6B, it was apparent that GFP was uniformly expressed throughout the mucosal subcutaneous tissue.

6-3. Evaluation of Therapeutic Effect by Dysosmia Behavior Test

The dysosmia behavior test was carried out by evaluating the time which it takes for a mouse to find a piece of cheese. Specifically, mice in which dysosmia was induced by methimazole were used as a dysosmia model. First, 150 mg/kg body weight of methimazole was intraperitoneally administered to mice to induce dysosmia in the mice. The dysosmia model mice (seven individuals) were individually placed in a cage 24 hours after methimazole administration and fasted for 24 hours. Micelles including mRNA encoding brain-derived neurotrophic factor (BDNF) were prepared by the same method as in Example 1 and 50 μL of the resultant micelle solution (containing 10 μg of the mRNA) was subjected to nasal drip on the nostril of the mice. Only a buffer was administered to control mice. The behavior test was carried out one day, three days, five days, seven days, and 10 days after the administration of the micelles. In this test, the mice were each fasted from 24 hours before the behavior test. A small piece of cheese was placed on a corner of the cage bedded 4 cm in thickness, and the time which it takes for the mouse to find and grasp or start to eat the cheese was measured. The test was performed by repeating four times at intervals of 10 minutes. The cutoff value for the time required was set at five minutes, and when the mouse could not find the cheese by that time, the time required was recorded as five minutes.

Figure 6C:
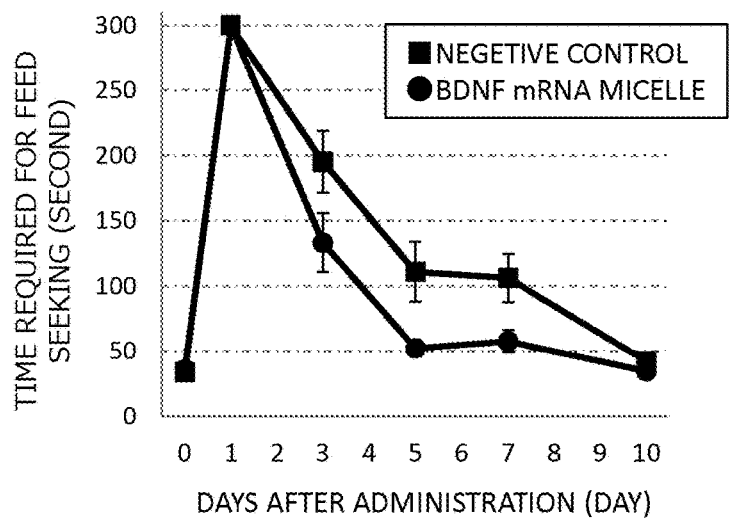

As a result, as shown in FIG. 6C, the time which it takes to find the cheese piece was significantly short in the mice to which the BDNF expression mRNA inclusion micelles were administered, compared to in the control mice, and the recovery rate was also improved.

6-4. Histological Evaluation of Therapeutic Effect

The therapeutic effect of mRNA inclusion micelles on dysosmia was histologically verified. Mice were euthanized and their heads were excised one day, seven days, 14 days, or 28 days after mRNA inclusion micelle administration. After demineralization, the head tissue was embedded in paraffin and tissue sections 5 μm in thickness were prepared. Thereafter, the sections were subjected to hematoxylin-eosin staining. Immunohistochemical staining was carried out for visualizing the expression of olfactory marker protein (OMP). A blocking solution containing a 1/5,000 dilution of goat anti-OMP antibody (Wako Chemical USA, Richmond, Va.) was used as a primary antibody and reacted with the sections at room temperature overnight, and a blocking solution containing a 1/400 dilution of Alexa546-conjugated secondary antibody (from Invitrogen) was used as a secondary antibody and reacted with the sections at room temperature for one hour. The nucleus was stained with roLong Gold Antifade Reagent with DAPI (from Invitrogen).

Figure 6D:
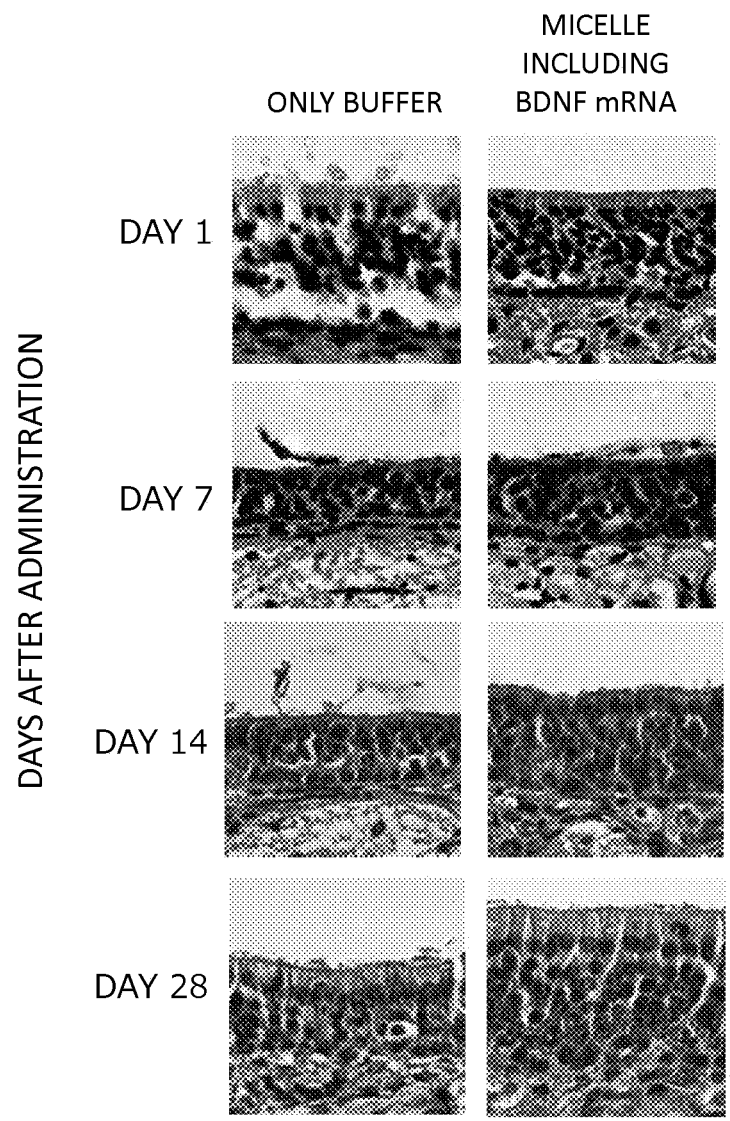
Figure 6E:
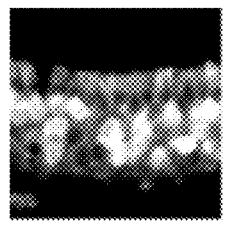

As a result, the distinct recovery of olfactory epithelium tissue and olfactory nerve was observed in a group to which micelles including mRNA encoding BDNF were administered, seven days, 14 days, and 28 days thereafter (FIG. 6D). The regenerated tissues also expressed OMP (FIG. 6E). This showed that nerve cells were efficiently recovered with the mRNA inclusion micelle of the present invention.

As just described above, the mRNA inclusion micelle of the present invention could achieve the therapy of the dysosmia model by nasal drip.

Example 7: Therapeutic Effect on Fulminant Hepatitis

In this Example, the therapy of fulminant hepatitis familiar from the broad induction of rapid cell death was attempted by administering micelles including mRNA encoding a factor suppressing apoptosis.

First, 5 μg of Jo-2 (BD Bioscience) as Fas ligand (FasL) was intraperitoneally administered to prepare a fulminant hepatitis model. Fifteen minutes after preparation, micelles including mRNA of Bcl-2 gene, plasmid DNA in which Bcl-2 gene was expressively incorporated, or saline was administered to the fulminant hepatitis mice as described above, and four hours after administration, the liver was harvested from the mice. Liver sections were prepared by the method described above and subjected to TUNEL stain treatment using an in situ cell death detection kit, TMR red (Roche, Basel, Switzerland). After observation with In Cell Analyzer 1000, the proportion of TUNEL-positive cells was quantified using software for In Cell Analyzer 1000. The number of cells per one field of vision was 2,000 on average, and five or more fields of vision per mouse were used for analysis.

Figure 7:
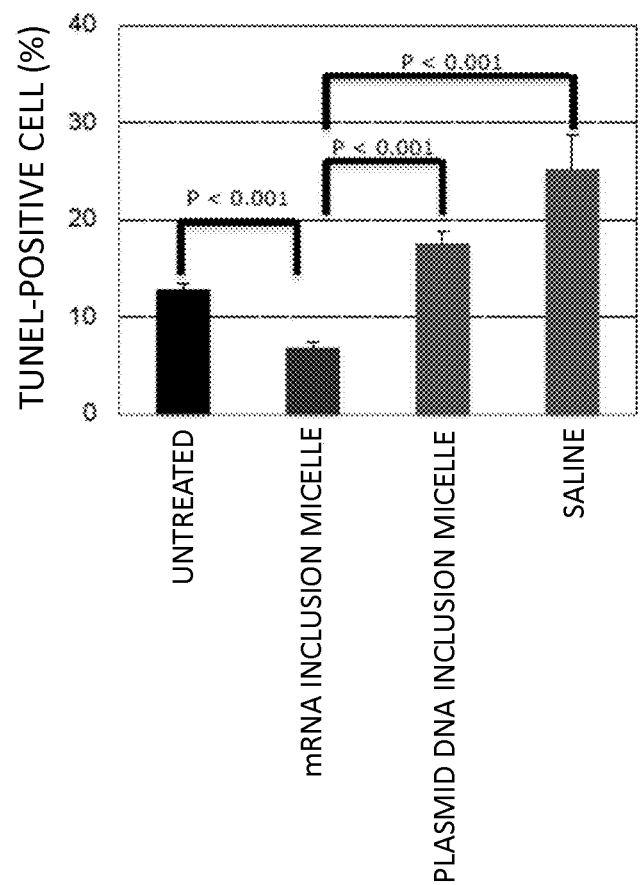
FIG. 7 is a graph showing the effect of the expression of Bcl-2 using mRNA inclusion micelles in fulminant hepatitis model mice.

As a result, the proportion of TUNEL-positive cells increased in a group to which saline was administered and a group to which the plasmid DNA was administered compared to an untreated group, rather resulting in worsening of the disease state, whereas the proportion of TUNEL-positive cells decreased in a group to which the mRNA inclusion micelles were administered, resulting in an improvement in disease state (FIG. 7).

These results suggest that the properties of the mRNA inclusion micelle enabling the uniform, rapid, and sustained expression of a protein in all cells were effective in the therapy of fulminant hepatitis familiar from the broad induction of rapid cell death.

As just described above, the mRNA inclusion micelle of the present invention is evaluated to provide a therapeutic method effective on diseases for each of which a wide range of cells are rapidly altered and the disease state is rapidly worsened.

mRNA has been considered to be not suited as a candidate for an introduced agent because of its strong immunogenicity and high instability. However, according to the present invention, the mRNA inclusion micelle unexpectedly has little immunogenicity and has provided a method for uniformly, rapidly and sustainedly expressing a protein in all cells in vivo. mRNA is expected as providing a gene therapy method safe in terms of causing no integration into a genome.

The invention claimed is:

1. A polyion complex comprising a cationic polymer and a messenger RNA (mRNA), wherein the cationic polymer is a polycation block of formula (I):

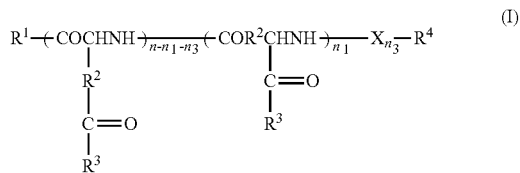

wherein
$R^1$ is a hydroxyl group, a protective group, or a polymerizable group;
$R^4$ is H, a protective group, a hydrophobic group, or a polymerizable group;
$R^2$ is methylene;
$R^3$ is a group represented by $-(NH-(CH_2)_2)_p-NH_2$;
X is any one amino acid selected from cationic natural amino acids;
p is any integer of 1 to 5;
n is any integer of 2 to 5,000;
$n_1$ is any integer of 0 to 5,000;
$n_3$ is any integer of 0 to 5,000;
$n-n_1-n_3$ is an integer of 0 or more,
although the repeating units in the formula are shown in the particular order for the purpose of description, the repeating units can be present in any order; the repeating units may be randomly present; and the repeating units may be the same or different,
wherein when the polycation block forms a copolymer with polyethylene glycol, $R^1$ or $R^4$ represents a bond and polyethylene glycol forms a copolymer with the polycationic block through $R^1$ or $R^4$ as the bond;
wherein $n-n_1-n_3$ or $n_1$ is an integer of 2 or more.

2. The polyion complex according to claim 1, wherein the polycation block is a polycation block of formula (II):

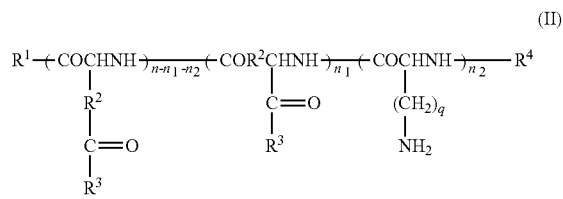

wherein
R1 is a hydroxyl group, a protective group, or a polymerizable group;
R4 is H, a protective group, a hydrophobic group, or a polymerizable group;
R2 is methylene;
R3 is a group represented by —(NH—(CH2)2)p-NH2;
p is any integer of 1 to 5;
q is any integer of 1 to 5;
n is any integer of 2 to 5,000;
n1 is any integer of 0 to 5,000;
n2 is any integer of 0 to 5,000;
n-n1-n2 is an integer of 0 or more,
although the repeating units in the formula are shown in the particular order for the purpose of description, the repeating units can be present in any order; the repeating units may be randomly present; and the repeating units may be the same or different, wherein when the polycation block forms a copolymer with polyethylene glycol, R1 or R4 represents a bond and polyethylene glycol forms a copolymer with the polycation block through R1 or R4 as the bond.

3. The polyion complex according to claim 1, wherein the mRNA is an mRNA encoding a growth factor, a cell growth factor, a cytostatic factor, a cell death promoter, a cell death suppressor, a tumor-suppressor gene product, or a transcription factor.

4. The polyion complex according to claim 3, wherein the cell growth factor is a hemopoietic factor or a brain-derived neurotrophic factor (BDNF).

5. The polyion complex according to claim 3, wherein the cell death suppressor is Bcl-2.

6. The polyion complex according to claim 1, wherein the mRNA comprises modified cytidine and uridine.

7. A method for delivering mRNA to the cytoplasm of a cell in the body of a subject, comprising administering the polyion complex according to claim 1 to a subject, wherein the mRNA is delivered to the cytoplasm of the cell.

8. The method according to claim 7 for uniformly expressing a protein in a tissue of a subject or portion thereof in the subject, comprising administering the polyion complex to the subject, wherein the tissue of the subject or portion thereof is perfused with the polyion complex.

9. The method according to claim 8, wherein the tissue is hepatic or mucosal tissue.

* * * * *